(12) United States Patent
Elmaanaoui

(10) Patent No.: US 10,816,789 B2
(45) Date of Patent: Oct. 27, 2020

(54) OPTICAL PROBES THAT INCLUDE OPTICAL-CORRECTION COMPONENTS FOR ASTIGMATISM CORRECTION

(71) Applicant: Canon U.S.A., Inc., Melville, NY (US)

(72) Inventor: Badr Elmaanaoui, Belmont, MA (US)

(73) Assignee: Canon U.S.A., Inc., Melville, NY (US)

(\*) Notice: Subject to any disclaimer, the term of this patent is extended or adjusted under 35 U.S.C. 154(b) by 0 days.

(21) Appl. No.: 15/879,319

(22) Filed: Jan. 24, 2018

(65) Prior Publication Data

US 2019/0227298 A1    Jul. 25, 2019

(51) Int. Cl.
| | |
|---|---|
| *G02B 23/24* | (2006.01) |
| *G02B 23/26* | (2006.01) |
| *G02B 23/06* | (2006.01) |
| *A61B 5/00* | (2006.01) |
| *A61B 1/07* | (2006.01) |
| *G01B 9/02* | (2006.01) |

(52) U.S. Cl.
CPC ............ *G02B 23/2423* (2013.01); *A61B 1/07* (2013.01); *A61B 5/0066* (2013.01); *A61B 5/0073* (2013.01); *A61B 5/0084* (2013.01); *G01B 9/0205* (2013.01); *G02B 23/06* (2013.01); *G02B 23/26* (2013.01)

(58) Field of Classification Search
CPC ................... G02B 23/2423; A61B 1/00177
See application file for complete search history.

(56) References Cited

U.S. PATENT DOCUMENTS

| | | |
|---|---|---|
| 5,509,917 A | 4/1996 | Cecchetti et al. |
| 5,554,100 A | 9/1996 | Leiner et al. |
| 6,433,937 B1 | 8/2002 | Konno |
| 6,445,939 B1 | 9/2002 | Swanson |
| 6,501,878 B2 | 12/2002 | Hughes |
| 6,564,087 B1 | 5/2003 | Pitris et al. |
| 6,620,154 B1 | 9/2003 | Amirkhanian et al. |
| 6,751,379 B2 | 6/2004 | Capewell et al. |
| 6,801,375 B2 | 10/2004 | Hayashide |
| 6,954,296 B2 | 10/2005 | Takakubo |
| 7,366,376 B2 | 4/2008 | Shishkov |
| 7,457,044 B2 | 11/2008 | Ohzawa |
| 7,492,987 B2 | 2/2009 | Yeik et al. |

(Continued)

FOREIGN PATENT DOCUMENTS

| | | |
|---|---|---|
| JP | H04-60608 A | 2/1992 |
| JP | H7-171162 A | 7/1995 |

(Continued)

OTHER PUBLICATIONS

Yu-Kuan Lu et al., Asymmetric elliptic-cone-shaped microlens for efficient coupling to high-power laser diodes, Optics Express, vol. 15, No. 4, Feb. 19, 2007.

(Continued)

*Primary Examiner* — Omar R Rojas
(74) *Attorney, Agent, or Firm* — Canon U.S.A., Inc. IP Division

(57) ABSTRACT

Some embodiments of a device comprise a light-guiding component; an optical-focusing component, wherein the light-guiding component and the optical-focusing component are aligned on an optical axis; and an optical-correction component that includes a reflecting surface and a correction surface.

30 Claims, 7 Drawing Sheets

(56) References Cited

U.S. PATENT DOCUMENTS

| | | | |
|---|---|---|---|
| 7,680,378 | B2 | 3/2010 | Alphonse |
| 7,813,609 | B2 | 10/2010 | Petersen |
| 8,180,134 | B2 | 5/2012 | Wang |
| RE43,875 | E | 12/2012 | Shishkov |
| 8,425,500 | B2 | 4/2013 | Hanley et al. |
| 8,515,221 | B2 | 8/2013 | Flanders |
| 8,582,934 | B2 | 11/2013 | Adler |
| 8,641,296 | B2 | 2/2014 | Nishimura |
| 8,781,287 | B2 | 7/2014 | Flanders |
| 8,971,679 | B2 | 3/2015 | Ho |
| RE45,512 | E | 5/2015 | Tearney |
| 9,036,966 | B2 | 5/2015 | Bhagavatula |
| 9,069,122 | B2 | 6/2015 | Takeuchi |
| 9,087,368 | B2 | 7/2015 | Tearney |
| 9,164,272 | B2 | 10/2015 | Maillard |
| 9,318,810 | B2 | 4/2016 | Zelenski |
| 9,488,782 | B2 | 11/2016 | Griffin |
| 9,662,173 | B1 | 5/2017 | Griffin |
| 10,234,676 | B1 | 3/2019 | Elmaanaoui |
| 2002/0076180 | A1 | 6/2002 | Miyano |
| 2004/0133071 | A1 | 7/2004 | Alekseenko et al. |
| 2005/0165315 | A1 | 7/2005 | Zuluaga |
| 2006/0067620 | A1 | 3/2006 | Shishkov |
| 2007/0159601 | A1 | 7/2007 | Ho et al. |
| 2007/0233396 | A1 | 10/2007 | Tearney |
| 2008/0013960 | A1 | 1/2008 | Tearney |
| 2009/0244545 | A1 | 10/2009 | Toida |
| 2009/0262361 | A1* | 10/2009 | Tanioka ............... A61B 5/0066 356/479 |
| 2009/0306477 | A1 | 12/2009 | Togino |
| 2011/0137124 | A1 | 6/2011 | Milner |
| 2011/0141759 | A1* | 6/2011 | Smith ................. A61F 9/008 362/553 |
| 2012/0101374 | A1 | 4/2012 | Tearney et al. |
| 2013/0235176 | A1 | 9/2013 | Miyano |
| 2014/0288417 | A1 | 9/2014 | Schmidtlin et al. |
| 2015/0025369 | A1* | 1/2015 | Bhagavatula ........ G01B 9/0205 600/425 |
| 2015/0378105 | A1 | 12/2015 | Godbout et al. |
| 2016/0274345 | A1 | 9/2016 | Ueno et al. |
| 2016/0299170 | A1 | 10/2016 | Ito et al. |
| 2017/0168232 | A1 | 6/2017 | Tearney et al. |
| 2017/0235126 | A1 | 8/2017 | DiDomenico |
| 2018/0070932 | A1 | 3/2018 | Tearney et al. |
| 2018/0256032 | A1* | 9/2018 | Takeuchi ............. G02B 23/243 |
| 2019/0196188 | A1 | 6/2019 | Hirata et al. |
| 2019/0223699 | A1 | 7/2019 | Wu |
| 2019/0223700 | A1 | 7/2019 | Elmaanaoui |
| 2019/0227297 | A1 | 7/2019 | Wu |

FOREIGN PATENT DOCUMENTS

| | | |
|---|---|---|
| JP | 2010-533049 A | 10/2010 |
| JP | 2011-147705 A | 8/2011 |
| JP | 2012-229976 A | 11/2012 |
| JP | 2013-524930 A | 6/2013 |
| JP | 2015-532179 A | 11/2015 |
| JP | 2016-202866 A | 12/2016 |
| WO | 2014/157645 A1 | 10/2014 |
| WO | 2015116939 A1 | 8/2015 |
| WO | 2016077252 A1 | 5/2016 |

OTHER PUBLICATIONS

SPIE, Gradient Index Lens, Optipedia, Internet Archive Wayback Machine, May 16, 2016, downloaded from http://web.archive.org/web/20160516035942/http://spie.org/publications/tt48_55_gradient_index_lens.

Zhen Qiu et al., New Endoscopic Imaging Technology Based on MEMS Sensors and Actuators, Micromachines 2017, Jul. 2017.

Tianshi Wang et al., Numerical Analysis of Astigmatism Correction in Gradient Refractive Index Lens Based Optical Coherence Tomography Catheters, Applied Optics, 51(21):5244-5252, Jul. 20, 2012.

Woonggyu Jung et al., Numerical Analysis of Gradient Index Lens-Based Optical Coherence Tomography Imaging Probes, Journal of Biomedical Optics, vol. 15(6), Nov. 2010.

D. Yelin et al., Three-dimensional miniature endoscopy, Nature, Oct. 19, 2006, pp. 765—vol. 443.

Max Born, et al., Principles of Optics: Electromagnetic Theory of Propagation, Interference and Diffraction of Light, 6th ed., Pergamon Press, 1980, pp. 169-174 and 214-217 (and title and copyright pages included) (The year of publication for this reference is sufficiently earlier than the effective U.S. filing date and any foreign priority date so that the particular month of publication is not in issue.).

Eugene Hecht, Optics, 4th ed., Pearson Eduction, Adelphi University, 2002, pp. 261-264 (and title and copyright pages included) (The year of publication for this reference is sufficiently earlier than the effective U.S. filing date and any foreign priority date so that the particular month of publication is not in issue.).

Frank L. Pedrotti, et al. Introduction to Optics, 2nd ed, Prentice-Hall, Inc. Upper Saddle River, New Jersey, 1993, pp. 98-100 (and title and copyright pages included) (The year of the publication for this reference is sufficiently earlier than the effective U.S. filing date and any foreign priority date so that the particular month of publication is not in issue.).

* cited by examiner

OPTICAL PROBES THAT INCLUDE OPTICAL-CORRECTION COMPONENTS FOR ASTIGMATISM CORRECTION

BACKGROUND

This application generally concerns optical probes.

An optical-imaging catheter or endoscope's optical system is usually fragile and therefore is often protected by a sheath. Astigmatism is caused in the optical system by the shape of the sheath. Astigmatism causes the foci of the beams of light in two orthogonal directions to converge at different distances with different beam sizes or to diverge in one direction while converging in another direction. Thus, astigmatism reduces the image quality of the optical system.

SUMMARY

Some embodiments of a device comprise a light-guiding component; an optical-focusing component, wherein the light-guiding component and the optical-focusing component are aligned on an optical axis; and an optical-correction component that includes a reflecting surface and a correction surface.

Some embodiments of a device comprise a light-guiding component; an optical-focusing component; and means for reflecting light received from the optical-focusing component and producing an optical power on a first axis that is orthogonal to a second axis.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Some optical-imaging devices (e.g., endoscopes) are configured to capture images from inside a subject, such as a human patient. These optical-imaging devices may include an optical probe, and the optical probe may include both a lens and a mirror at a distal tip. The lens and the mirror focus a beam of light, collect the beam of light, and guide the beam of light. Also, one or more optical fibers in the optical probe can be used to navigate the optical probe to an object (e.g., organs, tissues), deliver light to the object, and detect light that is reflected by the object. Furthermore, an optical-imaging device may include a sheath that encloses the optical probe.

For example, an optical probe that is configured for optical coherence tomography (OCT) can capture depth-resolved images of the blood vessels in the surface of an object. As the beam of light from the optical probe is rotated across the surface, cross-sectional images of the blood vessels in the surface are obtained. In order to acquire three-dimensional data, the optical probe can be translated longitudinally during the rotation to obtain images from a helical-scanning pattern. This helical scanning may be performed by pulling the tip of the optical probe back towards a proximal end while the optical probe is being rotated or by pushing the tip of the optical probe towards a distal end while the optical probe is being rotated.

The sheath may be transparent or mostly transparent so that the beam of light can travel through the sheath. The sheath has an optical power, although the optical power of the sheath is not very strong when the medium inside and the medium outside the sheath are the same (e.g., the media inside and outside the sheath are both air, the media inside and outside the sheath are both the same contrast agent). However, if the media are different, then the sheath has a stronger optical power. For example, if the medium inside the sheath is air and the medium outside the sheath is a contrast agent, then the sheath has a negative optical power in the sagittal direction. Additionally, the smaller the diameter of the sheath, the stronger the optical power of the sheath, and the greater the astigmatism caused by the sheath.

Figure 1:
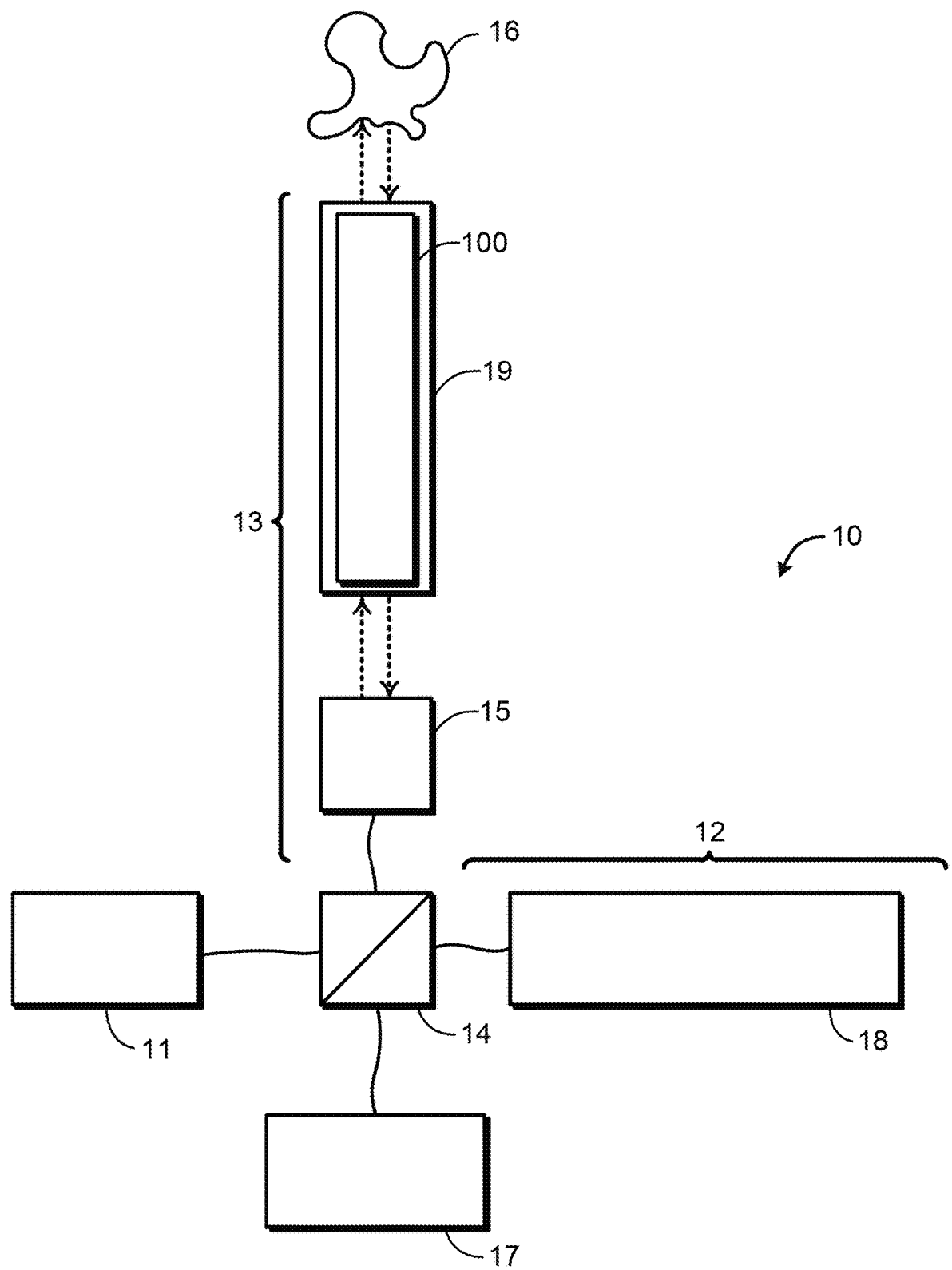
FIG. 1 illustrates an example embodiment of an OCT system.

FIG. 1 illustrates an example embodiment of an OCT system. The OCT system 10 includes a light source 11, a reference arm 12, a sample arm 13, a beam splitter 14, and one or more detectors 17. The light source 11 emits light, and the light source 11 may be, for example, a broad-band light source with a short coherence length, a superluminescent light-emitting diode (SLED), a tunable light source, and a white-light source. The beam splitter 14 splits the light, directs some of the light to the reference arm 12, and directs some of the light to the sample arm 13. Also, some embodiments of the system 10 use one or more circulators to split the light and use one or more beam couplers to recombine the light.

The sample arm 13 includes a patient-interface unit 15 and an optical-imaging device 19. The optical-imaging device 19 includes an optical probe 100, which directs a beam of light to a sample 16 and detects light that is reflected from or scattered by the sample 16. The optical probe 100 then transmits the reflected or scattered light back to the beam splitter 14.

The reference arm 12 includes an optical delay line 18. The optical delay line 18 includes a mirror, and light that travels through the optical delay line 18 is reflected off the mirror and travels back to the beam splitter 14.

The beams from the sample arm 13 and the reference arm 12 are recombined by the beam splitter 14, which generates a recombined beam that has an interference pattern. The recombined beam is detected by the one or more detectors 17 (e.g., photodiodes, photomultiplier tubes, a linear CCD array, an image sensor, a CCD array, a CMOS array).

Figure 2:
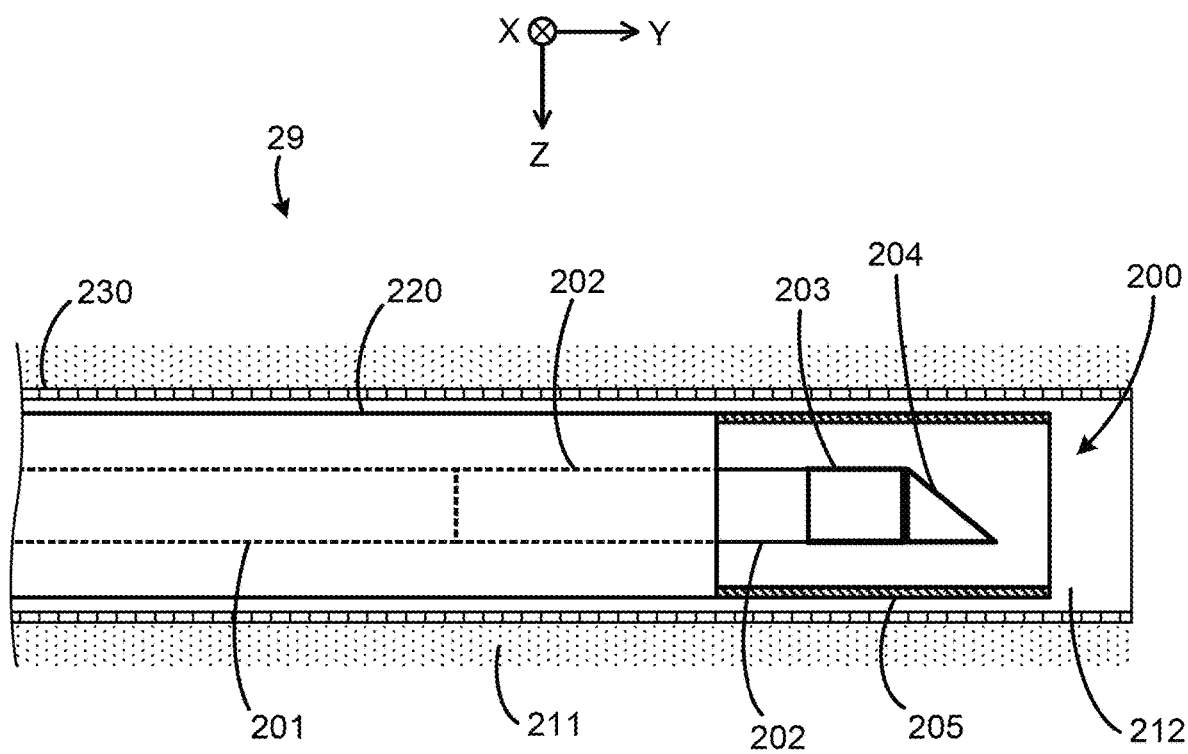
FIG. 2 illustrates a partially-cutaway view of an example embodiment of an optical-imaging device that includes an optical probe, a drive cable, and a sheath.

FIG. 2 illustrates a partially-cutaway view of an example embodiment of an optical-imaging device 29 (e.g., a catheter, an endoscope) that includes an optical probe 200, a drive cable 220, a protector 205, and a sheath 230. The optical probe 200 includes a first light-guiding component 201, which is a waveguide (e.g., a single-mode optical fiber, a multimode optical fiber, a double-clad optical fiber); a second light-guiding component 202, which is also a waveguide (e.g., a glass rod, a glass spacer, a large-core multimode fiber); an optical-focusing component 203 (e.g., a gradient-index (GRIN) lens, a ball lens, a half-ball lens, a graded-index (GI) fiber); and a light-reflecting component 204 (e.g., a prism). Also, the sheath 230 contains the protector 205, which surrounds part of the optical probe 200, and an inner medium 212 (e.g., air, a contrast agent), which is the medium inside the sheath 230. And the sheath 230 is surrounded by an outer medium 211 (e.g., air, a contrast agent), which is the medium outside the sheath 230. The sheath 230 may be mostly transparent or include a mostly-transparent window, and the sheath 230 may introduce a negative optical power along a first axis (the x axis in FIG. 2) and introduce almost no optical power along a second axis (the y axis in FIG. 2).

The drive cable 220, the protector 205, and the optical probe 200 are fixed relative to each other. The drive cable 220 delivers torque from its proximal end to its distal end in order to spin the distal end, which is attached to the optical probe 200. Spinning the optical probe 200 permits the optical probe to capture a 360° view.

Without correction, the optical-imaging device 29 may suffer from astigmatism caused by the sheath 230. The sheath's inner and outer surfaces are mostly flat in the tangential direction and thus have almost no influence on the optical power of the optical-imaging device 29. The sheath's inner and outer surfaces are curved in the sagittal direction. The inner surface has a negative optical power because, when air is the inner medium 212, light travels from the air to the concave inner surface of the sheath 230. The outer surface has a positive optical power because, when air is the outer medium 211, light travels from the concave outer surface of the sheath 230 to air. However, the optical power at the outer surface is not as strong as the optical power at the inner surface because the radius of the curvature of the outer surface is larger than the radius of the curvature of the inner surface. Also, the sheath's material typically has an index of refraction (IOR) in the rage of 1.3 to 1.6, which causes the optical power of the outer sheath to be weaker or slightly negative when the outer medium 211 is a contrast agent and not air. Some contrast agents have an IOR in the range of 1.43 to 1.47.

Figure 3A:
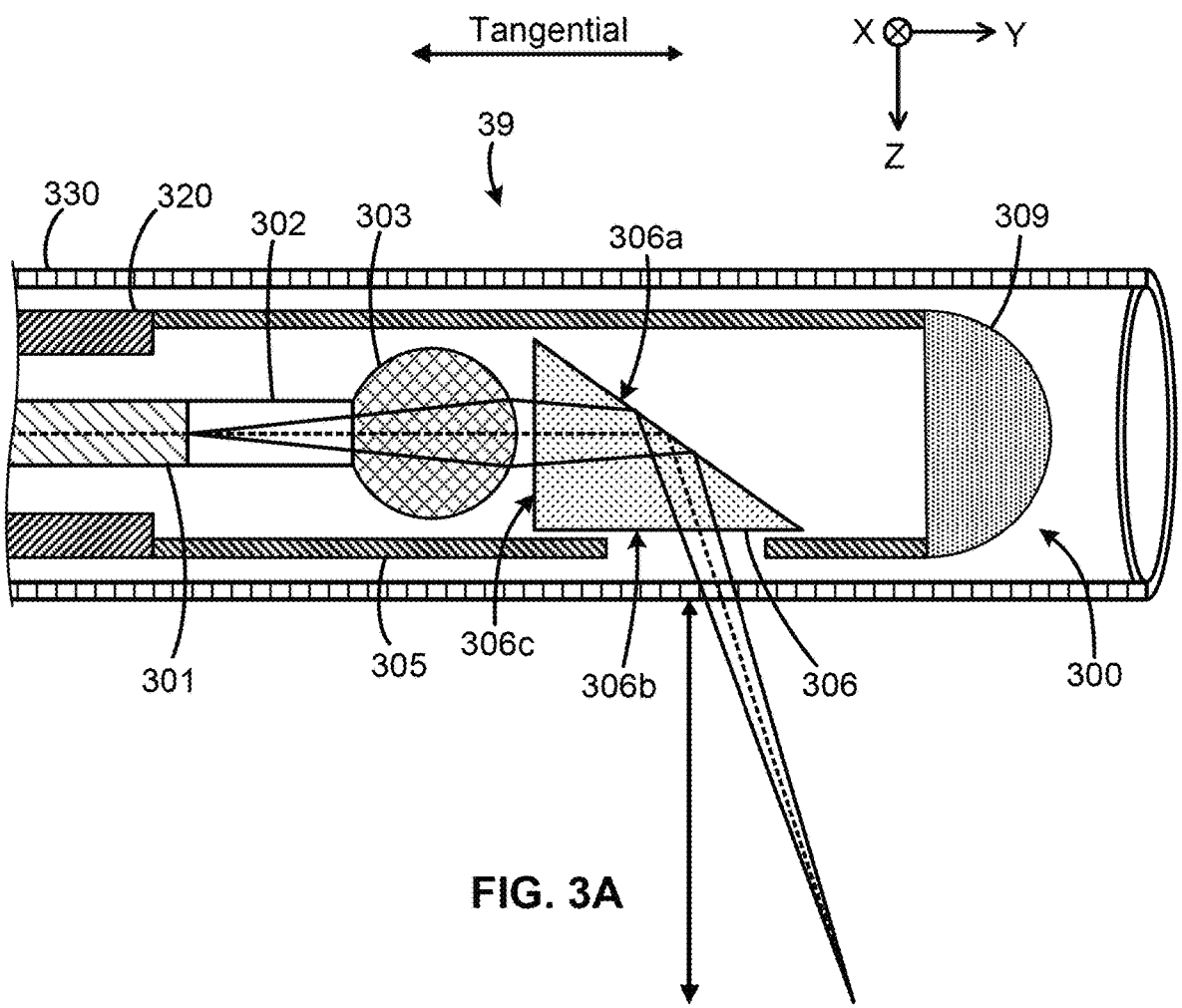
FIG. 3A illustrates a partially-cutaway view of an example embodiment of an optical-imaging device that includes an optical probe, a drive cable, and a sheath.

FIG. 3A illustrates a partially-cutaway view of an example embodiment of an optical-imaging device 39 that includes an optical probe 300, a drive cable 320, and a sheath 330. The optical probe 300 includes the following: a first light-guiding component 301, a second light-guiding component 302, an optical-focusing component 303, a protector 305, an astigmatism-correction and beam-steering component (ACBS) 306, and an atraumatic tip 309.

The first light-guiding component 301 and the second light-guiding component 302 are configured to deliver one or more beams of light to the distal tip of the optical probe 300. The first light-guiding component 301 may be, for example, a multi-clad fiber, a double-clad fiber, a multimode fiber, a polarization-maintaining fiber, or a single-mode fiber. The second light-guiding component 302 may be, for example, a glass rod, a large-core fiber, or another spacer that can be used to adjust the numerical aperture (NA) of a beam of light to the entrance of the optical-focusing component 303. By using glass-rod spacers of different lengths, the NA may be adjusted. Also, in some embodiments, the optical properties of the glass-rod spacer are adjustable, thereby allowing the NA to also be adjusted. And in some embodiments, an end face of the second light-guiding component 302 is fusion spliced to an end face of the first light-guiding component 301. Also, the y axis in FIG. 3A is aligned with a longitudinal axis of the first light-guiding component 301 or of the second light-guiding component 302.

In this embodiment, the optical-focusing component 303 is a ball lens that focuses a beam of light equally or nearly equally along orthogonal axes. Thus, the optical power of the ball lens may be equal or nearly equal on a first axis and on a second axis. Also, the optical-focusing component 303 may be attached to the second light-guiding component 302 or may be formed from an endface of the second light-guiding component 302, for example through a heating process.

The clear or mostly-clear sheath 330 (or window of the sheath 330) usually introduces a negative optical power along a first axis (e.g., the x axis in FIG. 3A) and almost no optical power along a second axis (e.g., the y axis in FIG. 3A).

Figure 3B:
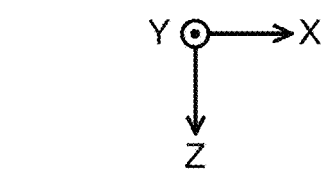
FIG. 3B illustrates an example embodiment of the astigmatism-correction and beam-steering component (ACBS) in FIG. 3A.
Figure 3C:
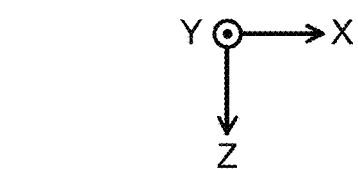
FIG. 3C illustrates an example embodiment of the ACBS in FIG. 3A.

In order to reduce or eliminate astigmatism, this embodiment includes an ACBS 306 that is not directly attached to the optical-focusing component 303. In the optical path, the ACBS 306 is located between the optical-focusing component 303 and the sheath 330. The ACBS 306 includes a reflecting surface 306a (e.g., a total-internal-reflection (TIR) surface) and has at least one correction surface 306b. In this embodiment, the correction surface 306b has a cylindrical curvature that introduces an optical power along one axis (e.g., the x axis in FIG. 3A). FIG. 3B illustrates an example embodiment of the ACBS 306 in FIG. 3A. The curvature of the correction surface 306b is visible in FIG. 3B. Additionally, FIG. 3C illustrates an example embodiment of the ACBS 306 in FIG. 3A. The curvature of the correction surface 306b is visible in FIG. 3C.

Also, in some embodiments, the ACBS 306 has an optical power on more than one of the two or three surfaces (e.g., the reflecting surface 306a, the correction surface 306b, and an entry surface 306c) that the light interacts with. Accordingly, in some embodiments, the reflecting surface 306a and the entry surface 306c are also correction surfaces. And the ACBS 306 may have an optical power on both a first axis and a second axis. In these embodiments, the delta power between the two optical powers and the optical powers of the optical-focusing component 303 can be configured to provide the desired beam parameters.

The spacing between the optical-focusing component 303 and the ACBS 306 may be used to adjust the optical power in one axis to adequately compensate for the astigmatism introduced by the sheath 330. In some embodiments, the spacing is approximately 10-350 µm. Also, the tips of the ACBS 306 may be chipped off in order to minimize the rigid-section length of the optical probe 300, mainly the protector 305.

In some embodiments, the angle of the reflecting surface 306b relative to the y axis is approximately 30-60°. For example, in some embodiments the angle is 53-58° to reduce back reflections from the sheath interface and to point the beam slightly forward.

The length of the ACBS 306 in the y direction can be chosen for ease of manufacturing and assembly. In some embodiments, the diameter of the ACBS 306 or the diameter of the optical-focusing component 303 matches, to within a tolerance, the internal diameter of the protector 305 for ease of alignment. Also, the material index of refraction of the ACBS 306 may be selected to provide the desired optical power to compensate for the sheath's optical power.

Figure 4A:
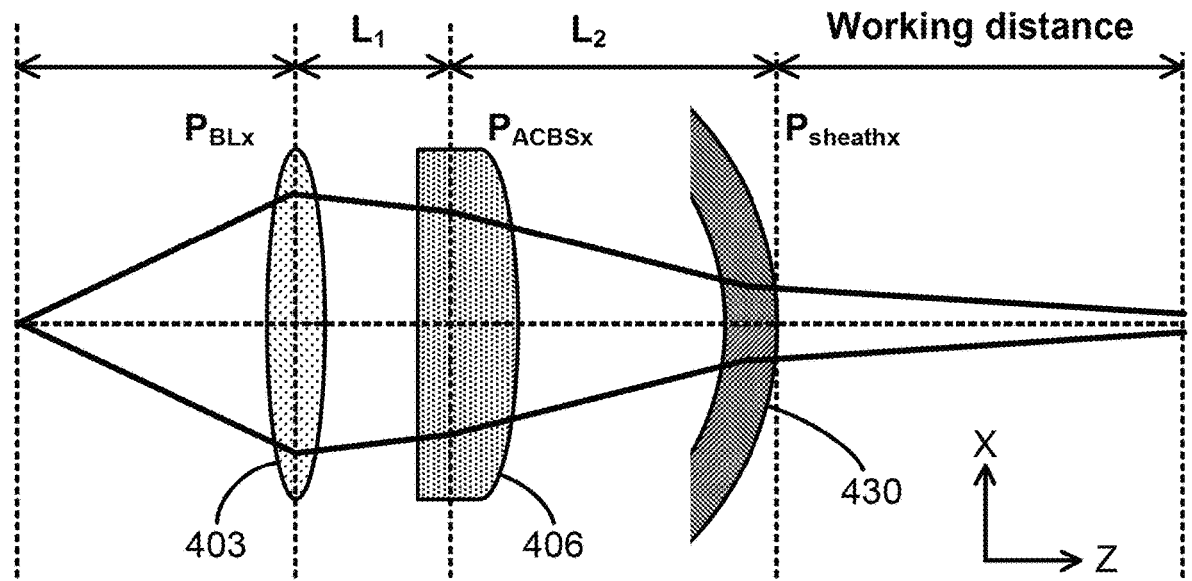
FIGS. 4A-B are conceptual illustrations that show the focusing of a beam of light in two orthogonal planes.
Figure 4B:
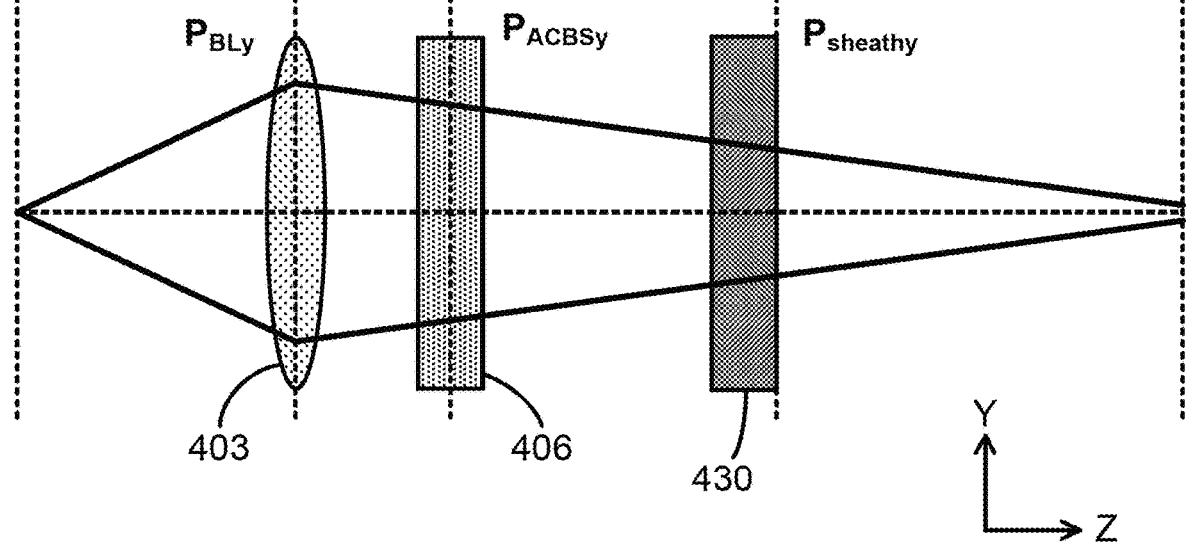

In some embodiments, the optical-focusing component 303 has an optical power on one axis that equals its optical power on another axis. Also, in some embodiments, the ACBS 306 has a positive optical power in the sagittal direction that compensates for the sheath's negative optical power in the sagittal direction. For example, in some embodiments, the optical-focusing component 303 can be described by $P_x = P_y = P_{Desired}$ (where $P_x$ is the power on the x axis, $P_y$ is the power on the y axis, and $P_{Desired}$ is the desired total power of the optical-imaging device 39), the ACBS 306 can be described by $P_x$=Positive P and $P_y$=0, and the sheath 330 can be described by $P_x$=Negative P and $P_y$=0. For simplicity, this notation assumes that the z axis is the axis of light propagation both before and after the reflection from the ACBS 306 (for example as illustrated in FIGS. 4A-4B), which eliminates the need to describe the axis change that is caused by the reflection of the ACBS 306.

And some embodiments include an ACBS 306 that has a negative optical power in the tangential direction that compensates for the sheath's negative optical power in the sagittal direction. For example, in some embodiments, the optical-focusing component 303 can be described by $P_x = P_y > P_{Desired}$ (where $P_x$ is the power on the x axis, $P_y$ is the power on the y axis, and $P_{Desired}$ is the desired total power of the optical-imaging device 39), the ACBS 306 can be described by $P_x$=0 and $P_y$=Negative P, and the sheath 330 can be described by $P_x$=Negative P and $P_y$=0. Again, for simplicity this notation assumes that the z axis is the axis of light propagation both before and after the reflection from the ACBS 306 (for example as illustrated in FIGS. 4A-4B), which eliminates the need to describe the axis change that is caused by the reflection of the ACBS 306.

Also, the components of the optical-imaging device 39 can be selected to suit a particular environment. Some embodiments of the optical-imaging device 39 are specially configured for use in an air environment, and some embodiments of the optical-imaging device 39 are specially configured for a liquid environment. The liquids that compose the liquid environment may include, for example, saline, dextran, water, or a combination of liquids. The optical-focusing component 303, the ACBS 306, and the sheath 330 may be selected according to the refractive index of the environment in which the optical-imaging device 39 will be used.

For example, in some embodiments, a beam of light with a center wavelength of 1.3 µm is delivered from a light source (e.g., the light source 11 in FIG. 1) through a first light-guiding component 301 that is an optical fiber made of Corning SMF-28ULTRA fiber and that has an outer diameter of 125 µm. After exiting the first light-guiding component 301, the light diverges through a second light-guiding component 302 that is a glass-rod spacer that is made of fused silica and has a diameter of 125 µm, which matches the outer diameter of the first light-guiding component 301. The length along the y axis of the second light-guiding component 302 (the glass-rod spacer in this example) is approximately 300 µm.

After the beam has been diverged by the second light-guiding component 302, the beam is converged nearly equally along a first axis and along a second axis by an optical-focusing component 303 that is a ball lens. The diameter of the ball lens is approximately 320 µm in this example. In some embodiments, the exit aperture of the ball lens may be anti-reflection (AR) coated to reduce back reflection.

The converged beam then propagates through air to the ACBS 306, is reflected by the reflecting surface 306a of the ACBS 306, and then travels through the correction surface of the ACBS 306. In this example embodiment, the correction surface 306b of the ACBS 306 has different optical powers ($P_x$, $P_y$) along different axes: $P_y$ is approximately zero, and $P_x$ is positive, for example when the correction surface 306b has a convex-cylindrical shape and is aligned with the cross-sectional direction z-x.

After the beam refracts from the correction surface 306b, it then passes through the sheath 330. In this example embodiment, the sheath 330 has an inner diameter of 600 µm, an outer diameter of 800 µm, and a refractive index of 1.50. Optically, the sheath 330 has a negative optical power along a first axis (e.g., the x axis in FIG. 3A) and zero optical power along a second axis that is orthogonal to the first axis (e.g., the y axis in FIG. 3A). Additionally, in this example, a contrast agent with a refractive index of 1.45 surrounds the outside of the sheath 330. This combination of the optical-focusing component 303 (the ball lens), the ACBS 306, and the sheath 330 causes the beam to focus at a working distance of approximately 2.1 mm from the outer surface of the sheath 330 (2.5 mm from the z axis along the center of the optical probe 300).

In contrast, using a ball lens that has a symmetric optical power and using an ACBS 306 that does not have a correction surface that has a positive optical power may cause the beam in the direction along the y axis to focus at a working distance of about 2.1 mm from the outer surface of the sheath 330 while causing the beam in the direction along the x axis to focus at a working distance of about 4.2 mm from the outer surface of the sheath 300. This happens due the negative optical power of the sheath 330 along the x axis. In this situation, the astigmatism of the sheath 330 causes the beam to focus at a distance on the x axis that is different from the focus distance on the y axis.

Furthermore, some embodiments of the optical probe 300 are configured to emit beams of light in more than one wavelength. For example, some embodiments that are configured for multimodal optical coherence tomography emit one beam that has a wavelength that is suitable for OCT and emit another beam that has a wavelength that is suitable for fluorescence imaging. The sizes of the members of the optical probe 300 and the arrangement of the members of the optical probe 300 may be configured to produce a desired beam width and a desired working distance.

Some embodiments of the optical probe 300 are configured for a multimodality system that simultaneously performs OCT imaging using light with a wavelength of 1.31 um and fluorescence mapping using light with a wavelength of 0.633 um. Depending on the specification of the imaging, it may be critical to focus the OCT wavelength, which can provide structural information, at a designed optimal working distance to provide lateral resolution, while the fluorescence wavelength is focused slightly off from the optimal working distance of the OCT imaging, thereby allowing the fluorescence wavelength to have a larger beam size with a lower lateral resolution at the optimal working distance of the OCT imaging.

For example, in coronary arteries, the diameters of the arteries of interest are often about 2 to 4 mm. Assuming that the optical probe 300 is located at the center of the artery, the radius of the artery corresponds to the working distance, and is 1 to 2 mm from the optical axis of the optical probe 300.

OCT and fluorescence wavelengths both penetrate the vessel, so, in some embodiments, the focus position or the working distance is optimal at 1 to 3 mm. Within these working distances, the focus may be different between the two modalities. Some embodiments of the optical probe 300 (e.g., for coronary-artery measurement) have focal distances or working distances that are within 2 mm of each other. Some embodiments have larger differences in the focal distances or working distances, for example embodiments that are used for larger blood vessels (e.g., peripheral arteries), corresponding to the blood vessel's diameter and the desired working distance.

The optimization of the focal point may be accomplished by using the refractive indices for the two wavelengths and solving the optimization problem. When optimizing, it may be efficient to add another material, with a different combination of refractive indices for the two wavelengths, by splitting one or more optical components or by adding a spacer.

Also, some embodiments of the optical probe 300 are configured for other modalities, such as near-infrared spectroscopy, in addition to or in alternative to OCT and fluorescence imaging.

FIG. 4A-B are conceptual illustrations that show the focusing of a beam of light in two orthogonal planes. FIGS. 4A-B are simplified illustrations that show only three members of an optical system: an optical-focusing component 403, an ACBS 406, and a sheath 430. FIG. 4A shows the three members in the x-z plane, and FIG. 4B shows the three members in the y-z plane. As shown by FIGS. 4A-4B, the optical power of the sheath 430 on the x axis is different than the optical power of the sheath 430 on the y axis. Also, the optical power of the ACBS 406 on the x axis is different than the optical power of the ACBS 406 on the y axis. In this example, the optical power of the ACBS 406 on the x axis is positive, and the optical power of the ACBS 406 on the y axis is zero or approximately zero. The optical power of the ACBS 406 compensates for the optical power of the sheath 430 so that the working distance on the x-z plane is the same or nearly the same (i.e., to within a tolerance) as the working distance on the y-z plane.

The optical system in FIGS. 4A-4B focuses the light at a working distance (W). The combined optical powers of the three members may be described by equation (1) and equation (2):

$$P_{y'} = P_{BL_y} + P_{ACBS_y} - P_{BL_y} P_{ACBS_y} L_1, \text{ and} \quad (1)$$

$$P_y = P_{y'} + P_{sheath_y} - P_{y'} P_{sheath_y} L_2;$$

$$P_{x'} = P_{BL_x} + P_{ACBS_x} - P_{BL_x} P_{ACBS_x} L_1, \text{ and} \quad (2)$$

-continued
$$P_x = P_{x'} + P_{sheath_x} - P_{x'} P_{sheath_x} L_2;$$

where $P_y$ is the total optical power along the y axis, where $P_x$ is the total optical power along the x axis, where $P_{BL_y}$ is the optical power of the optical-focusing component 403 along the y axis, where $P_{BL_x}$ is the optical power of the optical-focusing component 403 along the x axis, where $P_{ACBS_y}$ is the optical power of the ACBS 406 along the y axis, where $P_{ACBS_x}$ is the optical power of the ACBS 406 along the x axis, where $P_{sheath_y}$ is the optical power of the sheath 430 along the y axis, where $P_{sheath_x}$ is the optical power of the sheath 430 along the x axis, where $L_1$ is an optical distance between the optical-focusing component 403 and the ACBS 406, and where $L_2$ is an optical distance between the ACBS 406 and the sheath 430.

Also, the optical distance between the optical-focusing component 403 and the sheath 430 can be divided into a plurality of distances with respective refractive indices $n_j$, as described by the following:

$$L_i = \sum_{j=k}^{m} L_j n_j; i = 1, 2 \quad (3)$$

where i=1 ($L_1$) is the distance between the optical-focusing component 403 and the sheath 430, and where i=2 ($L_2$) is the distance between the ACBS 406 and the sheath 430.

Note that equations (1), (2), and (3) may be an oversimplification because, after the first two optical components, the second optical length $L_2$ may no longer be accurate to describe the final optical power once the third component is introduced. An optical-design-optimization tool may be used to adequately determine the properties of the optical components to reach a target total optical power that is mostly equal along both the first axis and the second axis.

In some embodiments, $P_{sheath_y}$ may be approximated with zero, and in some embodiments $P_{ACBS_y}$ may be approximated with zero. The optical powers may then be optimized such that $P_y \cong P_x$, which produces the following:

$$P_y \cong P_{x'} + P_{sheath_x} - P_{x'} P_{sheath_x} L_2. \quad (4)$$

The optical power of the sheath in the y direction ($P_{sheath_y}$) may be approximated using the thin-lens equation, as described below in equation (5), in which R is the inner diameter of the sheath 430 and ∆R is the thickness of the sheath 430:

$$P_{sheath_y} \cong \frac{-1}{R} + \frac{-1}{R + \Delta R} \cong \frac{-\Delta R}{R(R + \Delta R)}. \quad (5)$$

In some embodiments, the ACBS 406 compensates for the astigmatism caused by the sheath 430 such that the beam of light focuses at about the same working distance on the x axis and the y axis, which produces a small spot size.

Figure 5A:
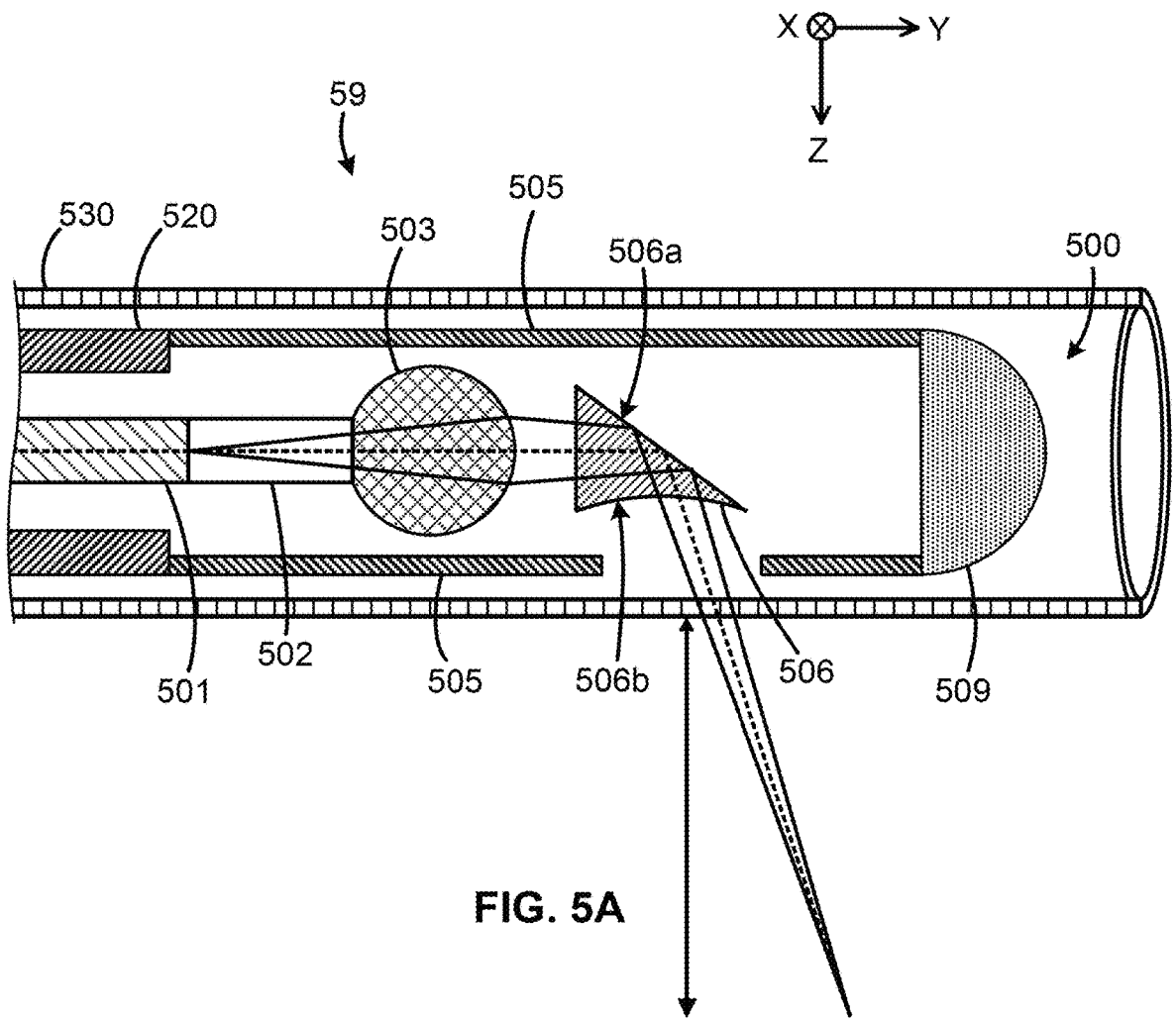
FIG. 5A illustrates a partially-cutaway view of an example embodiment of an optical-imaging device that includes an optical probe, a drive cable, and a sheath.

FIG. 5A illustrates a partially-cutaway view of an example embodiment of an optical-imaging device 59 that includes an optical probe 500, a drive cable 520, and a sheath 530. The optical probe 500 includes the following: a first light-guiding component 501, a second light-guiding component 502, an optical-focusing component 503, a protector 505, an ACBS 506, and an atraumatic tip 509.

Figure 5B:
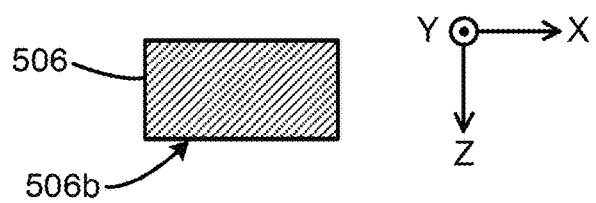
FIG. 5B illustrates an example embodiment of the ACBS in FIG. 5A.

In this embodiment, the ACBS 506 includes a reflecting surface 506a (e.g., a TIR surface) and includes a correction surface 506b. The correction surface 506b has a curvature that introduces and optical power. However, in this embodiment, the correction surface 506b has a curvature that produces a negative optical power on the y axis, but the correction surface 506b does not have an optical power on the x axis. The negative optical power of the ACBS 506 on the y axis may balance the negative optical power of the sheath 530 on the x axis. FIG. 5B illustrates an example embodiment of the ACBS 506 in FIG. 5A. The flatness of the correction surface 506b on the x axis is visible in FIG. 5B.

Also, the balanced positive optical power along both the x axis and the z axis of the optical-focusing component 503 may be increased to compensate for the negative optical powers introduced by the sheath 530 and the ACBS 506.

Figure 6A:
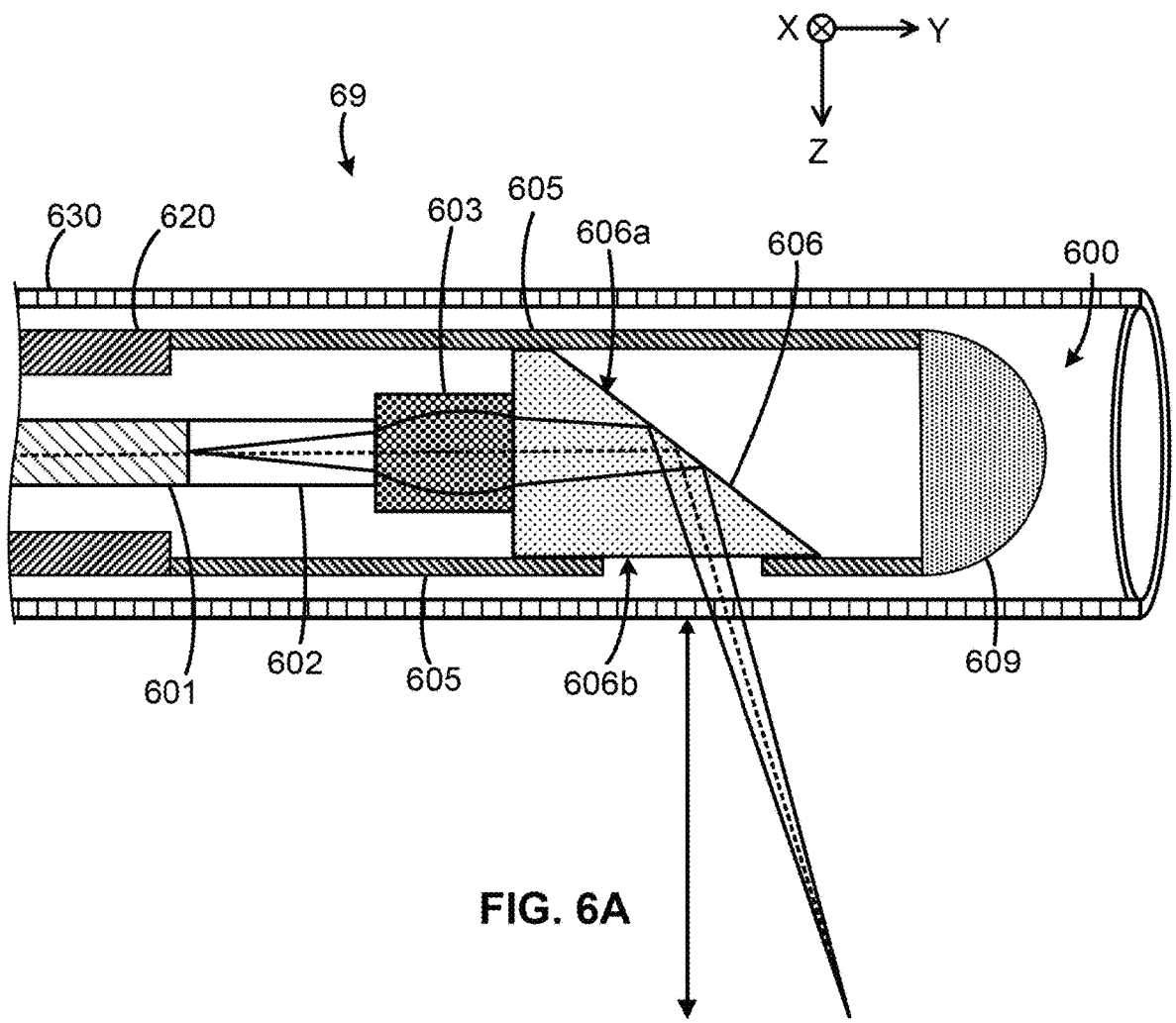
FIG. 6A illustrates a partially-cutaway view of an example embodiment of an optical-imaging device that includes an optical probe, a drive cable, and a sheath.

FIG. 6A illustrates a partially-cutaway view of an example embodiment of an optical-imaging device 69 that includes an optical probe 600, a drive cable 620, and a sheath 630. The optical probe 600 includes the following: a first light-guiding component 601, a second light-guiding component 602, an optical-focusing component 603, a protector 605, an ACBS 606, and an atraumatic tip 609.

The ACBS 606 includes a reflecting surface 606a and includes a correction surface 606b. Also, the ACBS 606 has a positive optical power in the sagittal direction that compensates for the sheath's negative optical power in the sagittal direction. The ACBS 606 may be an angle-cut, polished rod that is glued to the optical-focusing component 603, which is a gradient-index lens in this example embodiment.

Figure 6B:
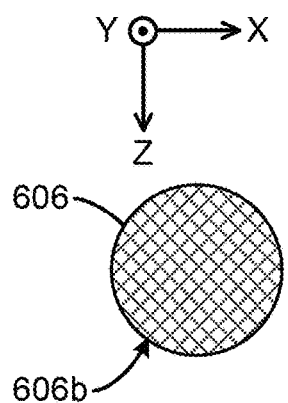
FIG. 6B illustrates an example embodiment of the ACBS in FIG. 6A.
Figure 6C:
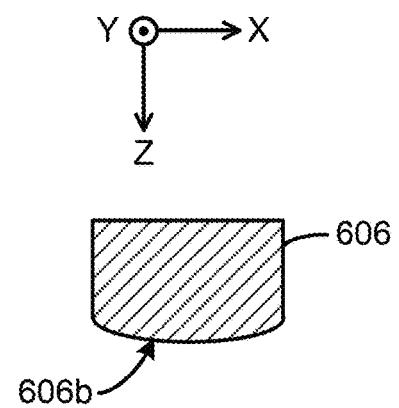
FIG. 6C illustrates an example embodiment of the ACBS in FIG. 6A.

FIG. 6B illustrates an example embodiment of the ACBS 606 in FIG. 6A. The curvature of the correction surface 606b is visible in FIG. 6B. Additionally, FIG. 3C illustrates an example embodiment of the ACBS 606 in FIG. 6A. The curvature of the correction surface 606b is visible in FIG. 6C.

Figure 7A:
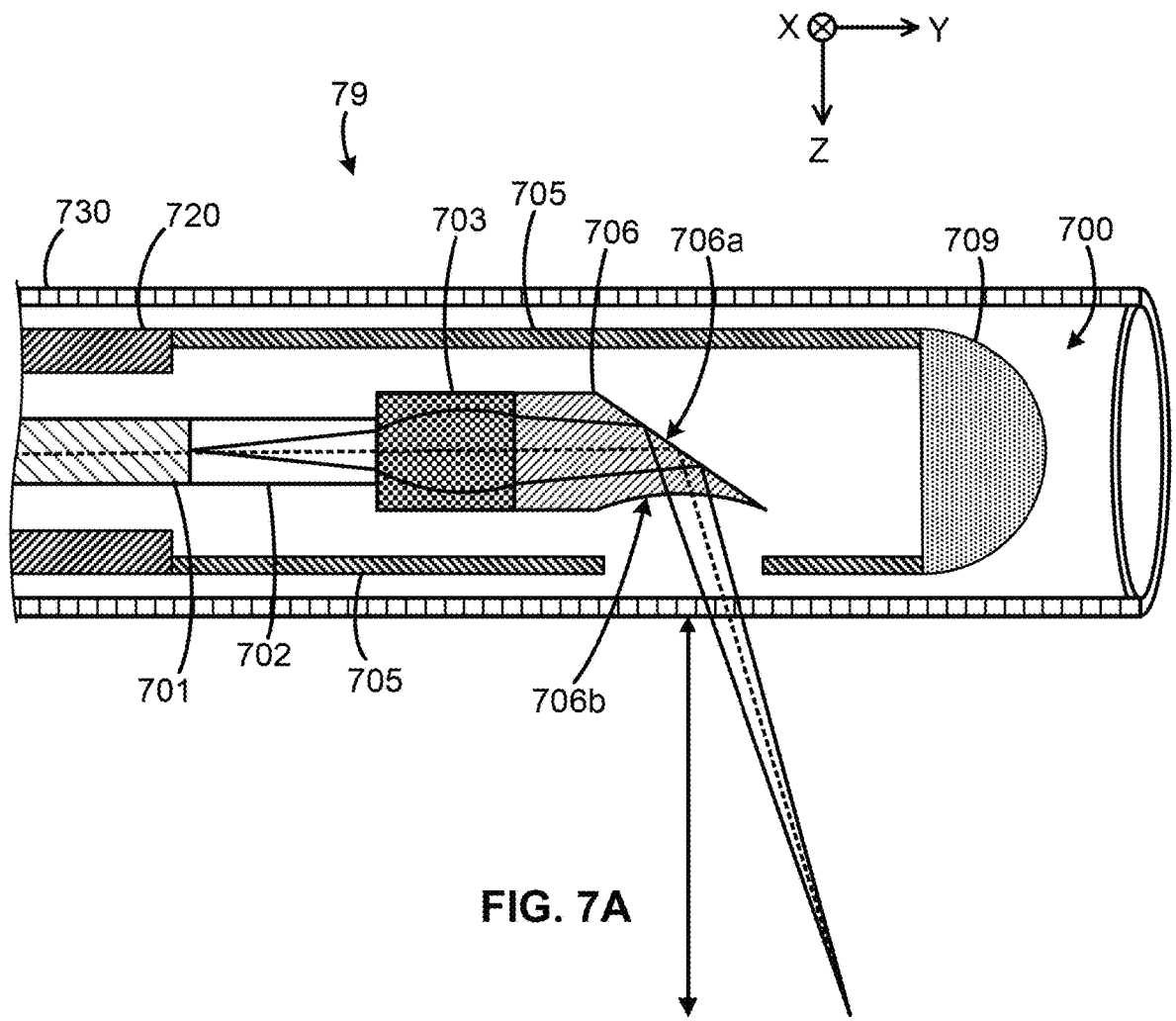
FIG. 7A illustrates a partially-cutaway view of an example embodiment of an optical-imaging device that includes an optical probe, a drive cable, and a sheath.

FIG. 7A illustrates a partially-cutaway view of an example embodiment of an optical-imaging device 79 that includes an optical probe 700, a drive cable 720, and a sheath 730. The optical probe 700 includes the following: a first light-guiding component 701, a second light-guiding component 702, an optical-focusing component 703, a protector 705, an ACBS 706, and an atraumatic tip 709.

Figure 7B:
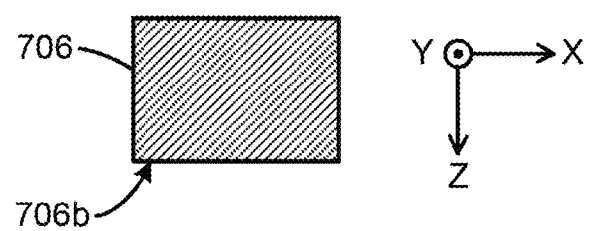
FIG. 7B illustrates an example embodiment of the ACBS in FIG. 7A.

In this embodiment, the ACBS 706 includes a reflecting surface 706a (e.g., a TIR surface) and includes at least one correction surface 706b that has a curvature that introduces an optical power. In this embodiment, the correction surface 706b has a curvature that produces a negative optical power on the y axis, but the correction surface 706b does not have an optical power on the x axis. The negative optical power of the ACBS 706 on the y axis may balance the negative optical power of the sheath 730 on the x axis. FIG. 7B illustrates an example embodiment of the ACBS 706 in FIG. 7A. The flatness of the correction surface 706b on the x axis is visible in FIG. 7B.

The ACBS 706 may be an angle-cut, polished rod that is glued to the optical-focusing component 703, which is a gradient-index lens in this example embodiment.

The scope of the claims is not limited to the above-described embodiments and includes various modifications and equivalent arrangements. Also, as used herein, the conjunction "or" generally refers to an inclusive "or," although "or" may refer to an exclusive "or" if expressly indicated or if the context indicates that the "or" must be an exclusive "or."

The invention claimed is:

1. A device comprising:
   a light-guiding component;
   an optical-focusing component, wherein the light-guiding component and the optical-focusing component are aligned on an optical axis;
   an optical-correction component that includes a reflecting surface and a correction surface, the correction surface operating to correct one or more optical aberrations; and
   a protector that: (i) surrounds at least a part of the optical-correction component, (ii) includes a hole or a window that operates to allow light reflected from the reflecting surface to pass through the hole or the window, and (iii) includes an atraumatic tip that: (a) operates to define, plug, or cap a part of a wall or boundary of the protector and/or (b) is spaced away from the optical-correction component,
   wherein:
   (i) the optical-correction component is spaced away from the optical-focusing component such that free space exists and extends between the optical-focusing component and the optical-correction component;
   (ii) the optical-correction component is in contact with or is directly attached to at least two opposite or different sides or portions of the protector; or
   (iii) the optical-correction component is in contact with or is directly attached to the optical-focusing component, the correction surface is concave along a length or an optical axis of the optical-correction component, and the optical-focusing component is spaced away from the protector such that free space exists and extends between the protector and the optical-focusing component.

2. The device of claim 1, wherein the reflecting surface is configured to direct light received from the light-guiding component toward the correction surface.

3. The device of claim 1, wherein the optical-focusing component is a gradient-index lens, a GI-fiber lens, a ball lens, or a half-ball lens.

4. The device of claim 3, wherein the optical-correction component is attached to the protector.

5. The device of claim 1, wherein the optical-correction component has an optical power on a first axis and has no optical power on a second axis that is orthogonal to the first axis.

6. The device of claim 5, wherein the optical-focusing component has an optical power on the first axis and an optical power on the second axis, and wherein the optical power on the first axis is equal to the optical power on the second axis.

7. The device of claim 5, further comprising:
   a sheath,
   wherein the sheath has a negative optical power on the first axis, and wherein the optical power on the first axis of the optical-correction component is positive.

8. The device of claim 5, further comprising:
   a sheath,
   wherein the sheath has a negative optical power on the second axis, and wherein the optical power on the first axis of the optical-correction component is negative.

9. The device of claim 1, wherein the light-guiding component, the optical-focusing component, and the optical-correction component are configured to transmit a first beam of light for optical coherence tomography and are configured to transmit a second beam of light for fluorescence imaging.

10. The device of claim 1, wherein the optical-correction component corrects an astigmatism in a wavelength of light for optical-coherence-tomography imaging.

11. The device of claim 1, wherein the optical-correction component corrects an astigmatism in a wavelength of light for fluorescence excitation.

12. The device of claim 1, wherein the optical-correction component corrects an astigmatism in a wavelength of light for optical-coherence-tomography imaging and wherein the optical-correction component corrects an astigmatism in a wavelength of light for fluorescence excitation such that a mean focal distance of the wavelength of light for optical-coherence-tomography imaging is within 2 mm of a mean focal distance of the wavelength of light for fluorescence excitation.

13. A device comprising:
a light-guiding component;
an optical-focusing component;
means for reflecting light received from the optical-focusing component, for optical corrections using a correction surface, and for producing an optical power on a first axis that is orthogonal to a second axis, the correction surface operating to correct one or more optical aberrations; and
a protector that: (i) surrounds at least a part of the means, (ii) includes a hole or a window that operates to allow light reflected from the means to pass through the hole or the window, and (iii) includes an atraumatic tip that: (a) operates to define, plug, or cap a part of a wall or boundary of the protector and/or (b) is spaced away from the means,
wherein:
(i) the means is spaced away from the optical-focusing component such that free space exists and extends between the optical-focusing component and the means;
(ii) the means is in contact with or is directly attached to at least two opposite or different sides or portions of the protector; or
(iii) the means is in contact with or is directly attached to the optical-focusing component, the correction surface is concave along a length or an optical axis of the means, and the optical-focusing component is spaced away from the protector such that free space exists and extends between the protector and the optical-focusing component.

14. The device of claim 13, wherein the optical power on the first axis is a positive optical power.

15. The device of claim 14, further comprising:
a sheath,
wherein the sheath has a negative optical power on the first axis.

16. The device of claim 13, wherein the optical power on the first axis is a negative optical power.

17. The device of claim 16, further comprising:
a sheath,
wherein the sheath has a negative optical power on the second axis.

18. The device of claim 1, wherein the device includes one or more of the following features:

(i) the protector is spaced away from the optical-correction component;
(ii) the correction surface and the reflecting surface are, define, or are on different sides of the optical correction component, or the correction surface and the reflecting surface are positioned such that the light reflected from the reflecting surface exits from the optical correction component via the correct surface; and/or
(iii) the protector surrounds at least a part of the optical-correction component on at least two sides of the optical-correction component.

19. The device of claim 1, wherein:
(i) the optical-correction component is in contact with the optical-focusing component, and the optical-correction component and the optical-focusing component are located inside the protector, or
(ii) a portion of the optical-focusing component is anti-reflection coated to reduce or avoid back reflection.

20. The device of claim 1, wherein the optical-correction component and the optical-focusing component are located inside the protector.

21. The device of claim 1, wherein the optical-focusing component is one or more of: (i) distinct or discrete from the optical-correction component; and/or (ii) touching or spaced away from the optical-correction component.

22. The device of claim 1, wherein the correction surface is an exit surface for the light and/or is on a side of the optical-correction component that is spaced away from the optical-focusing component.

23. The device of claim 1, wherein one or more of the following: the correction surface further operates to introduce an optical power, and/or the correction surface is concave along a length or an optical axis of the optical-correction component.

24. The device of claim 1, wherein one or more of the following: the correction surface further operates to introduce an optical power, and/or the correction surface is convex along a width or lateral axis of the optical-correction component.

25. The device of claim 1, wherein the one or more optical aberrations are one or more of the following: one or more astigmatisms, and/or one or more of the optical aberrations are one or more astigmatisms predominantly in one plane.

26. The device of claim 1, wherein the reflecting surface and the correction surface are integral with the optical-correction component.

27. The device of claim 13, wherein one or more of the following: the correction surface further operates to introduce an optical power, and/or the correction surface is concave along a length or an optical axis of the means.

28. The device of claim 13, wherein one or more of the following: the correction surface further operates to introduce an optical power, and/or the correction surface is convex along a width or lateral axis of the means.

29. The device of claim 13, wherein the one or more optical aberrations are one or more of the following: one or more astigmatisms, and/or one or more of the optical aberrations are one or more astigmatisms predominantly in one plane.

30. The device of claim 13, wherein the means for reflecting light and for optical corrections using the correction surface is integral with the correction surface.

* * * * *